United States Patent
Lavelle et al.

(10) Patent No.: US 7,789,915 B2
(45) Date of Patent: Sep. 7, 2010

(54) STENT FOR IMPLANTATION

(75) Inventors: Shay Lavelle, Annacotty (IE); Jessica W. Miller, St. Louis, MO (US)

(73) Assignees: Vance Products Incorporated, Spencer, IN (US); Cook Ireland Limited, Limerick (IE)

( * ) Notice: Subject to any disclaimer, the term of this patent is extended or adjusted under 35 U.S.C. 154(b) by 104 days.

(21) Appl. No.: 11/748,323

(22) Filed: May 14, 2007

(65) Prior Publication Data
US 2007/0276466 A1 Nov. 29, 2007

Related U.S. Application Data

(63) Continuation-in-part of application No. 11/218,210, filed on Aug. 31, 2005, now Pat. No. 7,550,012, and a continuation-in-part of application No. 11/513,445, filed on Aug. 30, 2006.

(60) Provisional application No. 60/713,151, filed on Aug. 31, 2005.

(51) Int. Cl.
*A61F 2/04* (2006.01)
*A61M 5/00* (2006.01)

(52) U.S. Cl. .................. 623/23.66; 623/23.7; 604/8

(58) Field of Classification Search ............ 623/1.16, 623/1.22, 1.27, 1.32, 1.33, 23.66, 23.7, 1.11–1.15, 623/1.17–1.21; 606/191–192, 194, 200; 604/8, 9
See application file for complete search history.

(56) References Cited

U.S. PATENT DOCUMENTS 2,264,988 A 12/1941 Lee
4,713,049 A 12/1987 Carter
4,813,925 A 3/1989 Anderson, Jr. et al.
4,913,683 A 4/1990 Gregory
4,930,496 A 6/1990 Bosley, Jr.
4,931,037 A 6/1990 Wetterman
4,957,479 A 9/1990 Roemer (Continued)

FOREIGN PATENT DOCUMENTS

CA 2264988 9/1999

(Continued)

OTHER PUBLICATIONS

International Search Report dated Jun. 9, 2005 for PCT Application No. PCT/US2005/009848.

(Continued)

*Primary Examiner*—Corrine M McDermott
*Assistant Examiner*—Andrew Iwamaye
(74) *Attorney, Agent, or Firm*—Brinks Hofer Gilson & Lione

(57) ABSTRACT

A stent is made from a coiled wire and is very smooth along its length and as well its ends. The stent is thus highly atraumatic to patients, and because of its smooth surfaces, it presents a surface to which it is difficult for microbes to cling. The stent may be used in a minimally invasive procedure, such as for a ureteral stent, and may also be used percutaneously. Similar stents may be used in other body areas, such as in draining the biliary tract, the gastro-intestinal tract, hepatic procedures, and in vascular procedures as well.

10 Claims, 9 Drawing Sheets

U.S. PATENT DOCUMENTS

| | | | |
|---|---|---|---|
| 5,323,768 A | | 6/1994 | Saito et al. |
| 5,334,185 A | | 8/1994 | Gisey et al. |
| 5,359,991 A | | 11/1994 | Takahashi et al. |
| 5,441,516 A | * | 8/1995 | Wang et al. ............... 606/198 |
| 5,554,189 A | * | 9/1996 | De La Torre ............ 623/23.66 |
| 5,558,643 A | | 9/1996 | Samson et al. |
| 5,582,619 A | * | 12/1996 | Ken ........................... 606/191 |
| 5,643,254 A | | 7/1997 | Scheldrup |
| 5,865,723 A | | 2/1999 | Love |
| 6,033,413 A | | 3/2000 | Mikus |
| 6,096,034 A | | 8/2000 | Kupiecki |
| 6,264,611 B1 | | 7/2001 | Ishikawa |
| 6,280,457 B1 | | 8/2001 | Wallace |
| 6,332,892 B1 | | 12/2001 | Desmond |
| 6,395,021 B1 | * | 5/2002 | Hart et al. .................. 623/1.15 |
| 6,458,119 B1 | | 10/2002 | Berenstein |
| 6,589,262 B1 | | 7/2003 | Honebrink et al. |
| 6,652,536 B2 | * | 11/2003 | Mathews et al. ............ 606/113 |
| 6,685,744 B2 | | 2/2004 | Gellman et al. |
| 6,733,536 B1 | | 5/2004 | Gellman |
| 6,736,839 B2 | | 5/2004 | Cummings |
| 6,746,489 B2 | | 6/2004 | Dua et al. |
| 6,770,101 B2 | | 8/2004 | Desmond |
| 6,887,215 B2 | | 5/2005 | McWeeney |
| 7,044,981 B2 | | 5/2006 | Liu |
| 7,412,993 B2 | * | 8/2008 | Tzeng ........................ 140/149 |
| 2001/0018574 A1 | | 8/2001 | Toledo et al. |
| 2002/0183852 A1 | | 12/2002 | McWeeney |
| 2003/0018306 A1 | * | 1/2003 | Bucay-Couto et al. ...... 604/265 |
| 2004/0078088 A1 | | 4/2004 | Gellman |
| 2004/0087886 A1 | * | 5/2004 | Gellman ......................... 604/8 |
| 2004/0127918 A1 | * | 7/2004 | Nikolchev et al. .......... 606/157 |
| 2004/0181186 A1 | | 9/2004 | Gellman et al. |
| 2004/0267213 A1 | | 12/2004 | Knapp |
| 2005/0075538 A1 | * | 4/2005 | Banik et al. ................. 600/141 |
| 2005/0222581 A1 | | 10/2005 | Fischer, Jr. et al. |
| 2005/0234388 A1 | | 10/2005 | Amos |
| 2005/0240278 A1 | | 10/2005 | Aliski et al. |
| 2006/0079926 A1 | * | 4/2006 | Desai et al. ................. 606/200 |
| 2006/0095050 A1 | | 5/2006 | Hartley et al. |
| 2007/0021840 A1 | | 1/2007 | Lopera |
| 2007/0050006 A1 | | 3/2007 | Lavelle |
| 2007/0078446 A1 | | 4/2007 | Lavelle |
| 2007/0078511 A1 | * | 4/2007 | Ehr et al. .................... 623/1.27 |
| 2007/0276466 A1 | | 11/2007 | Lavelle |
| 2008/0086215 A1 | | 4/2008 | St. Pierre |
| 2008/0133025 A1 | | 6/2008 | Daignault |
| 2008/0183299 A1 | | 7/2008 | Monga |
| 2008/0208083 A1 | | 8/2008 | Lin |

FOREIGN PATENT DOCUMENTS

| | | |
|---|---|---|
| DE | 20 2005 001 416 U1 | 5/2005 |
| EP | 0 213 748 A1 | 3/1987 |
| EP | 0 365 269 A1 | 4/1990 |
| EP | 0 365 269 B1 | 3/1994 |
| EP | 0 672 394 | 9/1995 |
| WO | WO 93/25265 | 12/1993 |
| WO | WO 97/24081 | 7/1997 |
| WO | WO 97/36536 | 10/1997 |
| WO | WO 03/079930 A1 | 10/2003 |
| WO | WO 2005/096915 A1 | 10/2005 |
| WO | WO 2007/027830 | 3/2007 |

OTHER PUBLICATIONS

Cook Urological: "Flexor® Ureteral Access Sheath," obtained at the Internet address: http://www.cookurological.com/products/ureteroscopy/5_02/5_02_17.html, Aug. 23, 2006, 2 pages.

Cook Urlogolical: "Flexor DL® Ureteral Access Sheath," obtained at the Internet address: http://www.cookurological.com/products/ureteroscopy/5_02/5_02_19.html, Aug. 23, 2006, 2 pages.

Cook Urological: "Cook 810 Set™ for Retrograde Stent Placement," obtained at the Internet address: file://C:\DOCUME~1\aevensen/LOCALS~1\Temp\V5WD0KUE.htm, Aug. 24, 2006, 1 page.

International Search Report from PCT application No. PCT/US2006/033944 dated Jan. 12, 2007.

Office Action dated Dec. 26, 2008 for U.S. Appl. No. 11/513,445.

International Search Report and Written Opinion dated Aug. 12, 2008, related application PCT/US2008/062837.

Office Action dated Sep. 26, 2008 for related U.S. Appl. No. 11/218,210.

Canadian Intellectual Property Office Examiner's Report dated Aug. 20, 2007 (4 pages).

International Preliminary Examination Report dated Mar. 13, 2008 for related PCT application PCT/US2006/33944.

Office Action dated Jun. 29, 2009 for related U.S. Appl. No. 11/513,445.

Office Action dated Jun. 8, 2009 for related U.S. Appl. No. 11/513,445.

Notice of Allowance dated Mar. 23, 2009 for related U.S. Appl. No. 11/218,210.

International Preliminary Report on patentability for related PCT/US2008/062837 dated Nov. 26, 2009.

* cited by examiner

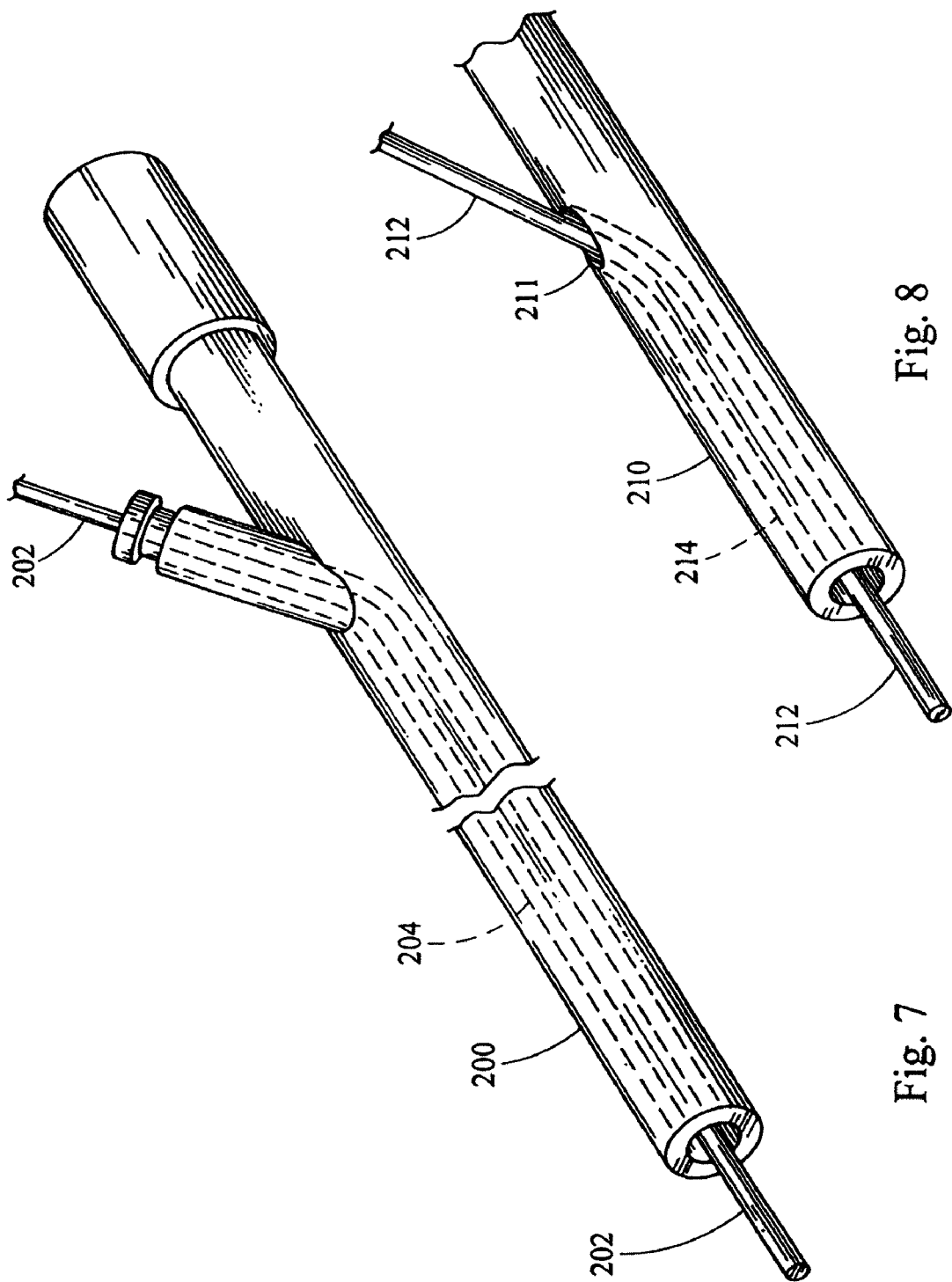

STENT FOR IMPLANTATION

RELATED APPLICATION

This application is a continuation in part of pending U.S. application Ser. No. 11/218,210 filed on Aug. 31, 2005, now U.S. Pat. No. 7,550,012, and is fully incorporated by reference herein. This application is a continuation in part of pending U.S. patent application Ser. No. 11/513,445 filed on Aug. 30, 2006, which claims priority from U.S Provisional Application No. 60/713,151 filed on Aug. 31, 2005 and is fully incorporated by reference herein.

TECHNICAL FIELD

The technical field of the invention is implantable medical devices, and in particular a stent useful for urinary drainage.

BACKGROUND

Minimally-invasive surgery has evolved to a point where procedures that were unimaginable a few years ago are now routinely performed on a daily basis. Even in these procedures, however, there is room for improvement. One example is the removal of stones and calculi from kidneys and ureters, to the great relief of many suffering patients.

To treat this condition, several individual steps are involved. In one procedure, these steps include placing a relatively narrow guidewire through a urethra and a bladder, and then through the ureter and into the kidney. After the guidewire is placed, a catheter is run along the guidewire, dilating the body passages (the urethra and the ureter) as it moves down the guidewire. In the next sequence for this procedure, a ureteral access sheath is guided along and down the guidewire and the catheter. The access sheath also dilates the body passages as it moves from outside the body, through the urethra, and into the ureter, down to the desired location, and into or very near the kidney.

The physician may then remove calculi and stones through the access sheath, using a grasper, a retrieval basket or other device. The access sheath protects the ureter from repeated passage of the retrieval device while the stones or calculi are removed. After the stones are removed, a ureteral stent may be placed into the ureter through the access sheath, using the catheter or a pushing tube to position the stent. The stent is used to retain patency of the ureteral lumen and to continue normal urinary drainage.

One problem with this procedure is that the guidewire may need to be very long in order for the physician to control passage first of the catheter and then of the access sheath to the desired location within the patient's body. Very long guide wires are not standard, and it may require two people to handle such a guide wire so that it does not drape onto the floor. The surgeon may decide he or she needs a guide wire with a stiffness different from the one provided with the particular kit in order to negotiate the pathway. A substitute stiffer guide wire may not be readily available in non-standard lengths.

Using this procedure for sequential placement of first a catheter and then an access sheath, the guidewire needs to be as long as the combination of both the catheter and the access sheath. A long guidewire leads to two problems, including a greater tendency to kink, and a need for greater skill on the part of the physician to maneuver the guidewire while placing the guidewire itself, the catheter, and the sheath.

Another problem that is encountered with ureteral stents occurs in cancer patients, where a growth may apply radial compression to a ureter. Such compression can make fluid flow difficult. In these cases, a typical polymeric, relatively soft pig-tail stent may not have sufficient radial strength to resist compression by a cancerous or other growth. In these cases, a stronger, sturdier ureteral stent is needed to resist radial compression and allow for continued drainage from the kidney to the bladder. In some cases, a urethral stent or catheter may also be helpful to ensure drainage from the bladder. What is needed is a better way to dilate the body passages in order to place the access sheaths and stents.

BRIEF SUMMARY

A first representative embodiment is a kit for placing a stent. The kit includes a wire guide and a stent for placing in a body passage of a patient. The stent includes a distal end portion and a proximal end portion, and a first hollow coiled wire defining a first lumen. The first lumen communicates outside the coiled wire through small spaces between adjacent coils. The stent further includes a second hollow coiled wire defining a second lumen, the second coiled wire is disposed within the first lumen and secured to the first hollow coiled wire.

A second representative embodiment is a stent. The stent includes a first hollow coiled wire with a first lumen between a distal end portion and a proximal end portion. The first lumen communicates outside the first coiled wire through small spaces between adjacent coils. A second hollow coiled wire is provided with a second lumen disposed within the first lumen and secured to the first hollow coiled wire.

Another embodiment is a method of preparing a stent suitable for implantation. The method includes steps of winding a wire coil, inserting a rod into the wound coil, attaching at least one end cap to the coil or to the rod, and electropolishing the stent. There are many embodiments of the kit and stents according to the present invention, of which only a few are described herein. The accompanying drawings and descriptions are meant to be illustrative rather than limiting.

BRIEF DESCRIPTION OF THE DRAWINGS

FIG. 7 is a catheter configured as a rapid exchange system;

FIG. 8 is a catheter configured as a rapid exchange system;

DETAILED DESCRIPTION OF THE DRAWINGS AND THE PRESENTLY PREFERRED EMBODIMENTS

Figure 1:
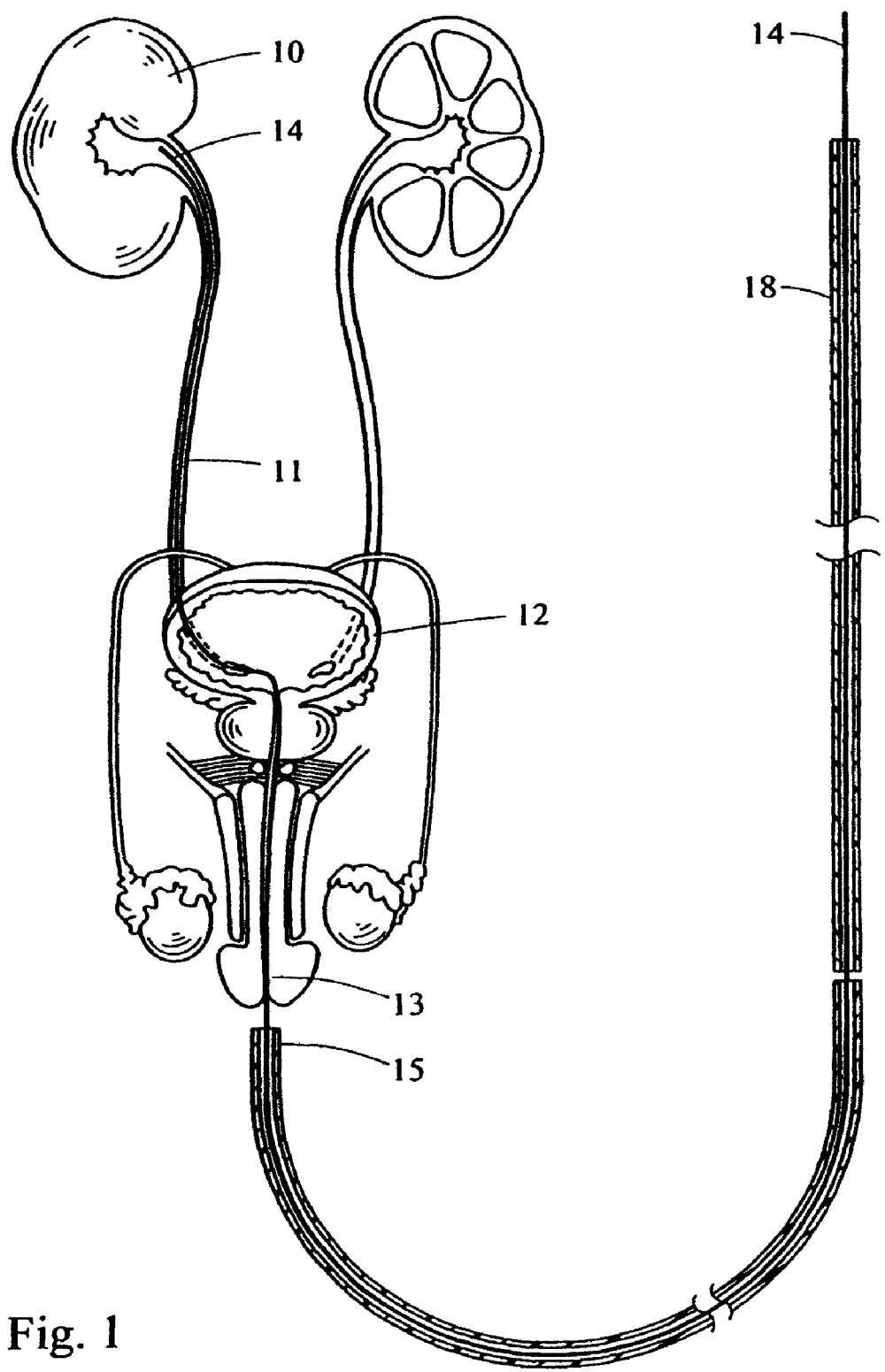
FIG. 1 is an illustration of a present technique for ureteral stent placement.
Figure 2:
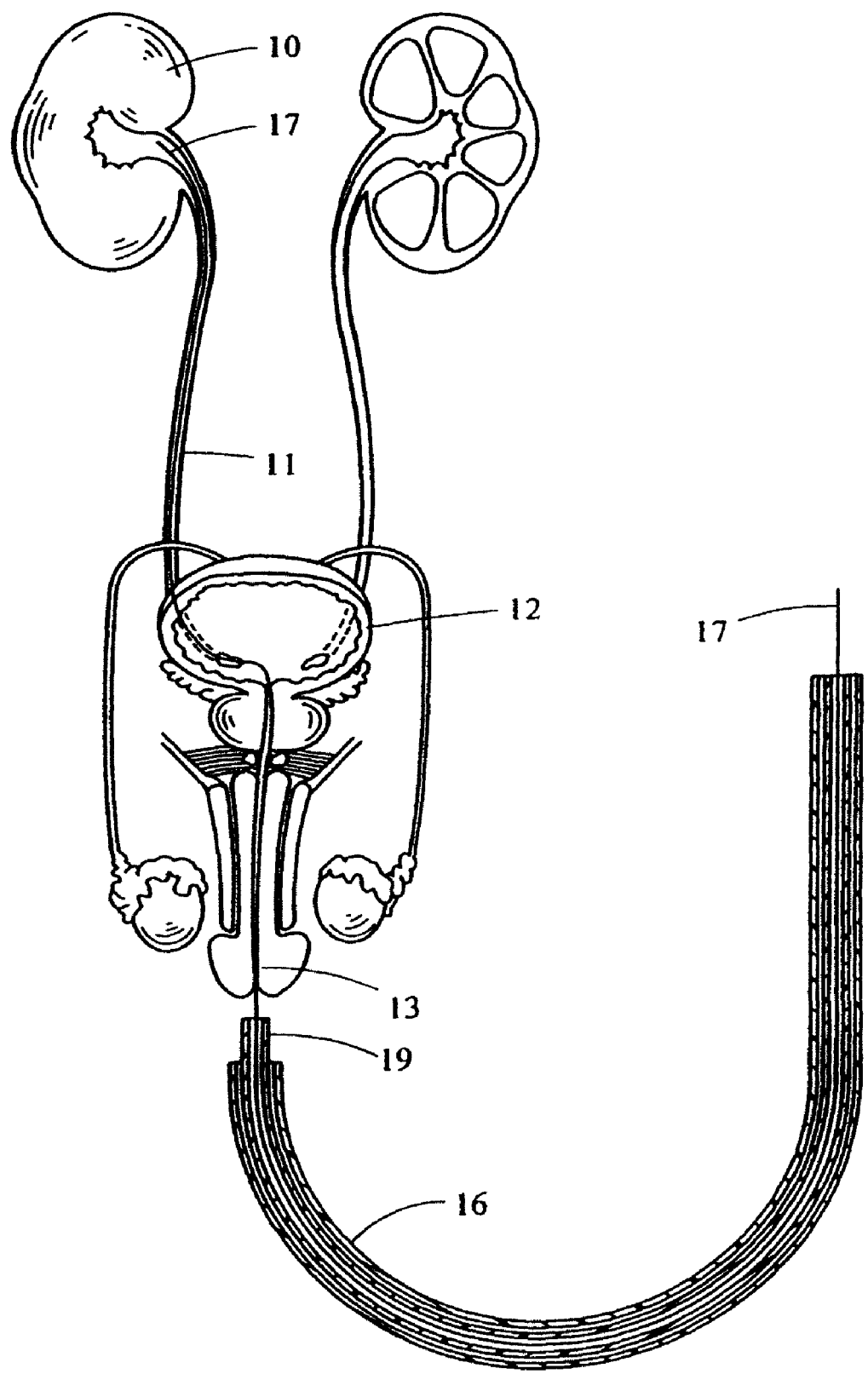
FIG. 2 is an illustration of a technique for dual dilatation.

FIGS. 1 and 2 illustrate the differences in technique between a present method for ureteral stent placement and a new method of coaxial dual dilatation. In both figures, a physician desires to perform a procedure upon a kidney 10. In FIG. 1, a guidewire 14 is advanced through a urethra 13, a bladder 12, and a ureter 11 to the kidney on which the procedure is to be performed. In order to accomplish this, the wire guide is placed, and a ureteral stent 15 is guided along the guidewire, extending as far as desired, typically into the kidney by means of a pushing tube 18 that is also placed along the guidewire as shown. The physician places the stent by passing first the guidewire, and then passing the ureteral stent and the pushing tube over the guide wire. The urethra may be dilated separately to accommodate an instrument such as a cystoscope to aid the surgeon.

The guide wire is typically between 0.018 to 0.038 inches in diameter (about 0.46 mm to 0.97 mm). The catheter may be 4-8 Fr. The ureteral stent may be used for patency of the ureteral lumen. In order to achieve this dilatation, however, a very long wire guide was needed to extend the length of the both the catheter and the access sheath, where the access sheath is capable of extending to the ureteropelvic junction. This may lead to kinking and may also lead to difficulty in the physician controlling the wire guide as he or she must control the entire length of the wire guide while sequentially running the catheter and the access sheath down the wire guide.

An improved method is illustrated in FIG. 2. In this method, a physician places a wire guide 17 through a urethra 13, a bladder 12, and a ureter 11 into a kidney 10. After the wire guide is placed, a catheter 19 secured to an access sheath 16 is guided along the wire guide, the catheter and access sheath combination coaxially "dual dilating" at least the proximal portion of the ureter. This coaxial dilatation procedure enables the physician to use a shorter wire guide, e.g., using a 145 or 150 cm wire guide rather than a wire guide that may have to be 220 cm or even longer, perhaps 250-260 cm. This may also shorten the time required to position the access sheath, and thus shorten the actual time spent in the therapeutic procedure and reduce the number of personnel required. The access sheath and the catheter are advanced to the desired location, e.g., into the calices of a kidney. The catheter may then be removed and replaced by a stent. The stent is then implanted by a surgeon pushing on a stent positioner, such as a catheter or other pushing device of appropriate diameter and length. The sheath-is then retracted while the positioner or other device is used to keep the stent in place.

In addition to the method shown in FIG. 2, there are other ways to practice the invention. For instance, rather than accessing the ureter through the urethra and bladder, a physician may use a nephrostomy method, in which the access sheath and catheter are advanced through a person's skin to reach the calices of the kidney directly. If a path to a bile duct is needed, the physician may access the bile duct through an endoscope via the mouth, esophagus, stomach and intestines, or via laparoscopic methods directly through the skin (percutaneous). If vascular access is desired, a physician may access the blood vessel through an opening, such as an opening manufactured in the femoral artery.

Figure 3:
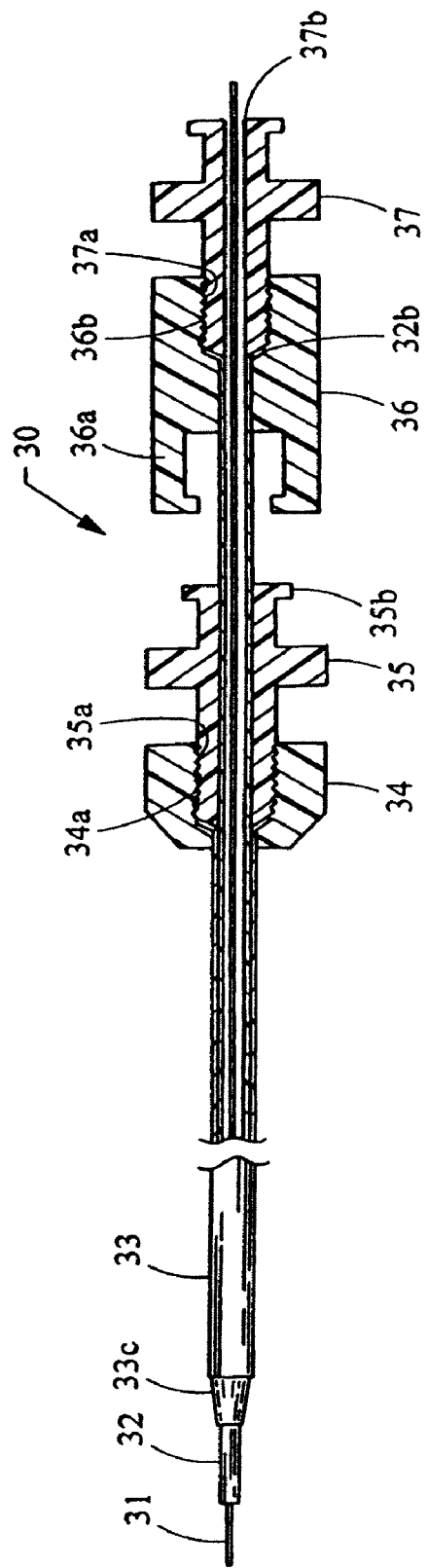
FIG. 3 is a cross-sectional view of a first embodiment of a kit according to the present invention.
Figure 3A:
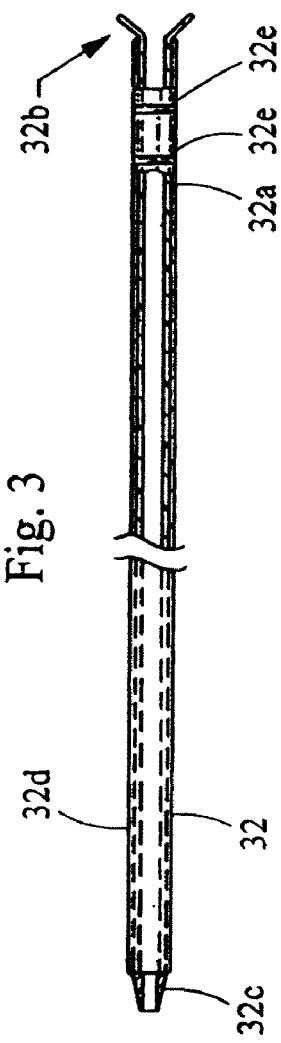
FIGS. 3a and 3b depict a catheter and a sheath useful in kit embodiments.
Figure 3B:
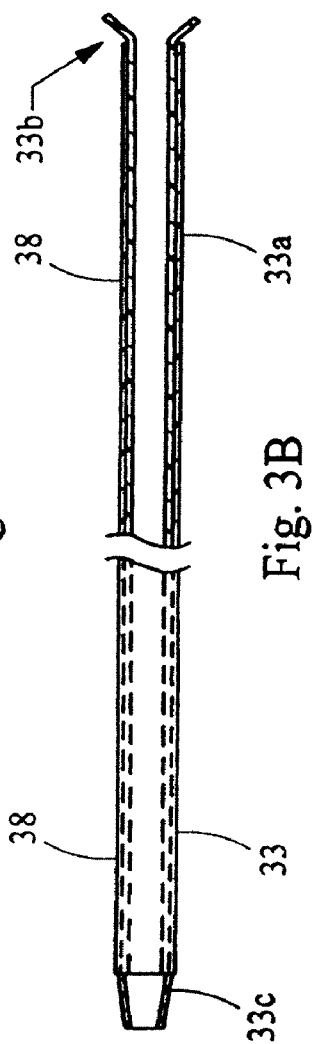

An embodiment of a kit useful in the above procedure is depicted in FIGS. 3, 3a and 3b. The kit includes a wire guide 31, which may be shorter than a wire guide used for a sequential procedure as described above. A wire guide with a length of about 145-150 cm is preferred, but other lengths may be used. A catheter 32 is included, the catheter preferably having a proximal end 32a with a flared tip 32b, and a soft rounded/tapered non-traumatic tip 32c for protection of the patient. Materials for the catheter are typically plastic or elastomeric materials, e.g., PVC, PTFE, polyurethane, silicone, and urethane, but any medically acceptable materials may be used. Catheters suitable for this use are preferably about 50-85 cm long. The tip is flared for ease in securing to connectors and in sealing with connectors so that the catheter may deliver a fluid, such as a radiopaque fluid for diagnostic procedures or for visualization purposes. The catheter may have a hydrophilic coating 32d on at least part of its outer surface. The proximal portion may also have one or more marking bands 32e to assist the physician in deploying the stent.

Catheter 32 may interface with one or more connectors 36 for mating with syringe adapter 37 (such as a female Luer lock adapter) so that a syringe (not shown) can inject the radiopaque fluid. Connector 36 may include a male Luer lock fitting 36a on a distal end of connector 36 and internal threads 36b on its proximal end. Male Luer lock connection 36a may be used to connect first connector 36 to second connector 35. Threads 36b may interface with matching external threads 37a of syringe adapter 37 for delivery of a fluid through lumen 37b. Flared end 32b of the catheter helps to seal the connection between connector 36, catheter 32, and syringe 37. While the Luer lock and threaded connections depicted and described are preferred, other connectors may be used instead. For example, quick-release connectors could be used to secure the catheter or sheath to their proximal fittings. When connectors 36 and 37 are joined with flared end 32b, a leak-tight connection is formed, and the catheter may reliably deliver fluid without undesirable leakage.

Access sheath 33 includes a proximal portion 33a and an end portion with a flared tip 33b. The access sheath also includes a distal end 33c, preferably atraumatic, soft and rounded or tapered for ease of introduction into the patient. Distal end 33c of the access sheath is also preferably more highly radiopaque than the remainder of the access sheath, so that the end may be observed with x-ray or fluoroscopic detection means during the implantation procedure. Flared tip 33b helps to seal an interface between access sheath 32 and connector 34. Access sheaths are preferably are made from low friction polymers (e.g. PTFE, FEP etc.) with reasonable radial compressive strength—wire reinforcement can be added to the sheath for extra radial strength. Suitable access sheaths sold under the name of Check-Flo® II Introducer sheaths sold by Cook Incorporated, Indiana may be used. Also Flexor® sheaths available from Cook Urological Incorporated of Spencer, Ind. may be used. In this application the sheath is typically 70 cm long so to extend from the urethral meatus to the ureteropelvic junction. The access sheath is generally just slightly larger in inner diameter than the outer diameter of the catheter, e.g. 0.5 Fr. If catheter 32, as shown in FIG. 3 and preferably with a blunt distal tip, is the same size diameter as the stent, the catheter may be used as a stent positioner, with the physician simply butting the distal end of the catheter against the proximal end of the stent so that the positioner can be used to push the stent into position.

Connector 34 may include internal threads 34a for connecting to Luer lock connector 35 having female Luer lock connection 35b. While Luer lock connections and connectors are preferred, other connectors and other types of medically-acceptable connectors may be used. At least a distal portion of sheath 33 may also include a hydrophilic coating 38.

The fittings described above may be used to connect access sheath 32 with catheter 33. To help insure that access sheath 32 seals securely, connector 34 may be temporarily joined to connector 35 with an adhesive. Other methods may also be used, such as securely tightening connectors 34, 35 together. Joining the female Luer lock connection 35b to male Luer lock connection 36a reliably secures access sheath 32 to catheter 33 for insertion or for removal. By breaking the connection between connectors 35, 36 after insertion, catheter 32 may be removed and the access sheath may be used for other purposes. These other purposes may include diagnostic purposes, such as insertion of an endoscope, or therapeutic procedures, such as breaking up stones or calculi, using a holmium laser or other type of lithotripter. A grasper or basket may then be inserted into the working channel of the endoscope to remove the fragments. In the same manner, connectors 36, 37 may also be temporarily joined with an adhesive to prevent easily breaking the connection. By adhering connector pairs 34, 35 and 36, 37, it is easier for the surgeon to make and break the Luer lock connection between connectors 35, 36.

In the assembled view of FIG. 3, note that the catheter may be longer than the access sheath, and may extend slightly further distally than the access sheath. Nevertheless, the sheath and the catheter are substantially coaxial, i.e., catheter 32 runs the entire length of access sheath 33. Substantially coaxial means that substantially the length of one of the sheath and the catheter is coaxial with the other of the sheath and the catheter during the procedure for implanting a stent or other device into a human or mammalian body.

In addition, the catheter (and/or the access sheath) can be configured to be a "rapid exchange" system. A rapid exchange system, also known as a "short wire guide" or "monorail" system, is an alternative technique for guiding a delivery catheter to a target site in a patient body by utilizing catheters having a relatively short wire guide lumen. In such systems, the wire guide lumen extends only from a first lumen opening spaced a short distance from the distal end of the catheter to a second lumen opening at or near the distal end of the catheter. As a result, the only lumenal contact between the catheter's wire guide lumen and the wire guide itself is the relatively short distance between the first and second lumen openings. Several known advantages are conferred by this configuration. For example, the portion of the wire guide outside the patient's body may be significantly shorter than that needed for the "long wire" configuration. This is because only the wire guide lumen portion of the catheter is threaded onto the wire guide before directing the catheter through the desired path (e.g., a working lumen of the access sheath, etc.) to the target site.

By way of illustration, FIGS. 7 and 8 illustrate the distal ends of two different types of catheters. FIG. 7 shows the distal end of long-wire catheter shaft 200 with a wire guide 202 disposed in a lumen 204. The lumen 204 extends substantially to the proximal end of the catheter shaft 200. (Note: The wire guides illustrated throughout this specification are drawn to illustrate the concepts being described and may not be shown to scale; preferred wire guides typically have an external diameter that is nearly the same as the internal diameter of catheter lumens through which they are passed.)

FIG. 8 shows the distal end of short-wire catheter shaft 210 with a side port aperture 211 and wire guide 212 disposed in lumen 214. The length of lumen 214, and consequently the exchange length of catheter 210, is substantially shorter than that of catheter 200 shown in FIG. 7. In addition to a shorter exchange length, catheter 210 (FIG. 8) has a reduced surface contact between the wire guide and catheter lumen that results in a reduced friction between the two. This can result in an eased threading and exchange process by reducing the time and space needed for catheter exchange. This economy of time and space is advantageous for minimally invasive surgeries by reducing the likelihood of contamination and reducing the total time and stress of completing surgical procedures.

In certain rapid exchange catheter configurations, the wire guide lumen is open to a side port aperture in the side of the catheter between its proximal and distal ends. In one such configuration, the wire guide lumen only extends from the side port aperture to an opening at the distal end. An example of this type of rapid exchange catheter is illustrated in FIG. 8.

Figure 9:
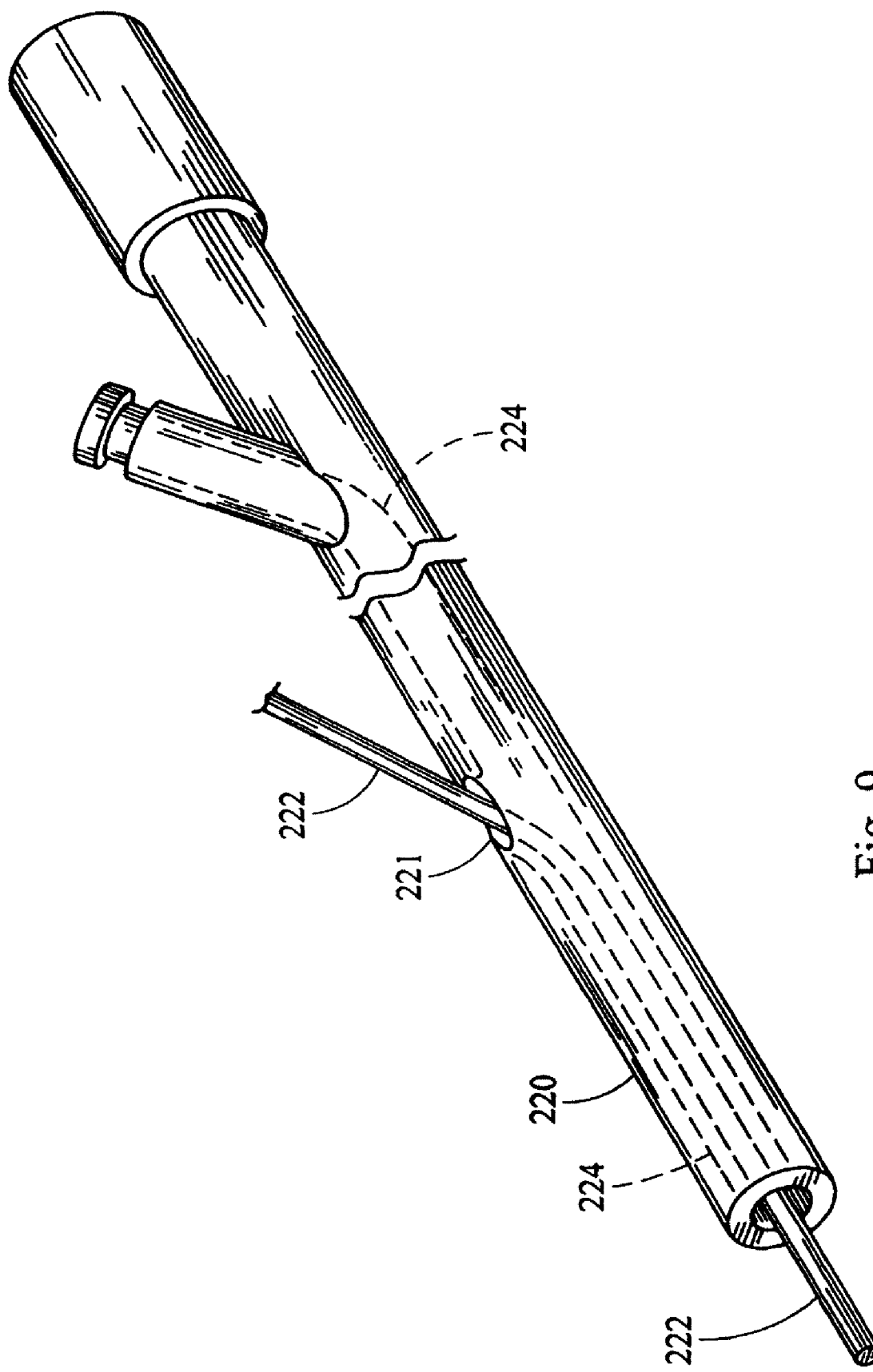
FIG. 9 is a catheter configured as a rapid exchange system.
Figure 10:
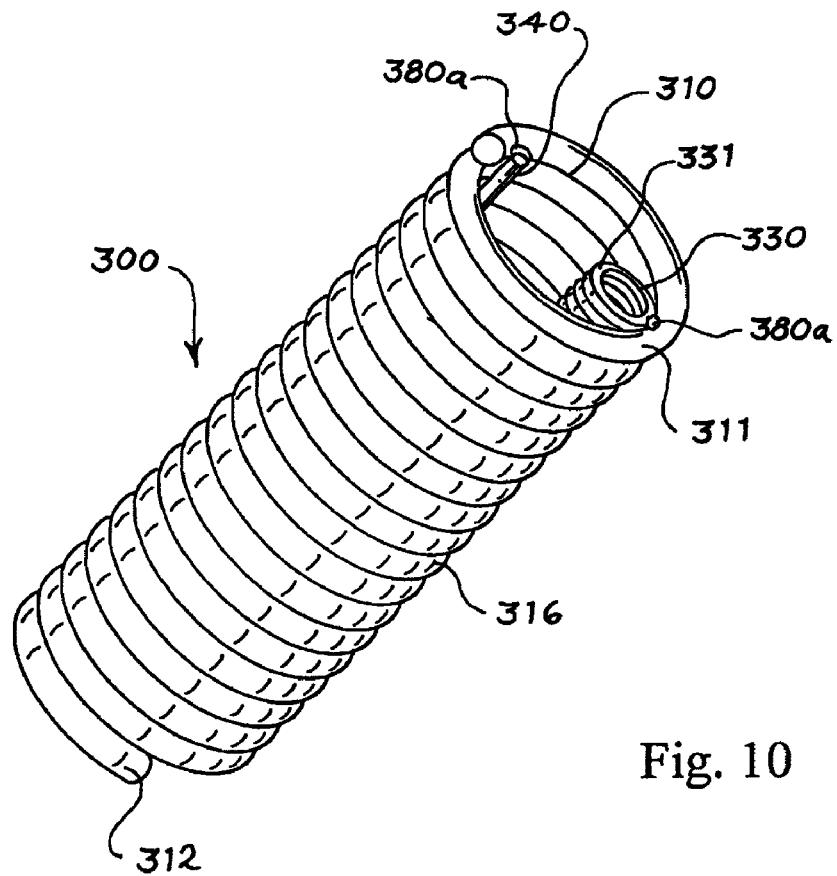
FIG. 10 is a perspective view of a dual lumen ureteral stent.

In another type of rapid exchange catheter configuration, the wire . guide lumen extends through the length of the catheter from near its proximal end to its distal end. A side port aperture between the proximal and distal ends opens into the wire guide lumen. This side port aperture allows the catheter to be used in a short wire guide configuration, while the full-length wire guide lumen allows the catheter to be used in a long wire guide configuration. This wire guide lumen configuration is referred to as "convertible" or "dual use." An example of this type of catheter is illustrated in FIG. 9, which shows the distal end of "convertible" catheter shaft 220 with wire guide 222 disposed through a side port aperture 221 and into a wire guide lumen 224. Specifically, a wire guide may run through substantially the entire length of the wire guide lumen, or the wire guide may run only through the portion of the lumen between the distal end and the side port aperture. The use of a rapid exchange system is not limited to catheters; it is contemplated that an access sheath can also benefit from that which is disclosed herein.

Figure 4:
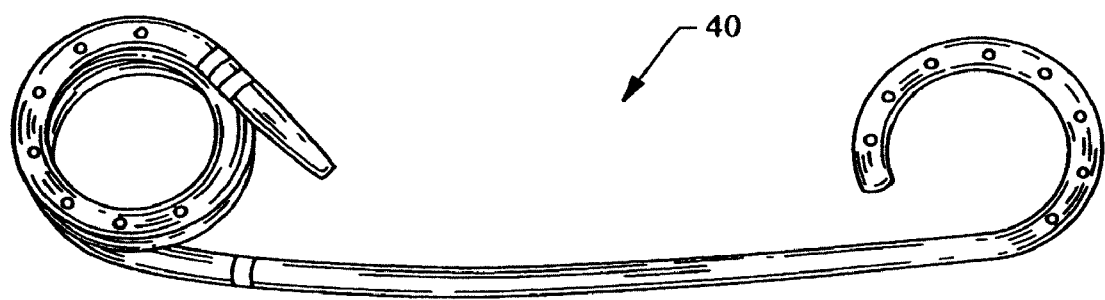
FIG. 4 depicts a pigtail ureteral stent.

The access sheath may also be used to place a ureteral stent when the above diagnostic or therapeutic procedures are completed. No matter how gentle the procedures described above, there is a chance of some amount of trauma to the ureter during the procedures. Accordingly, it may be prudent to place a stent into the ureter to maintain patency of the ureteral lumen. Ureteral stents may be of the "double pigtail" variety, such as those available from Cook Urological Incorporated, Spencer, Ind. FIG. 4 depicts one such stent 40. These ureteral stents are typically available in sizes of 4 Fr to 8 Fr and may be placed into a ureter using a wire guide and the procedure described above.

Figure 6:
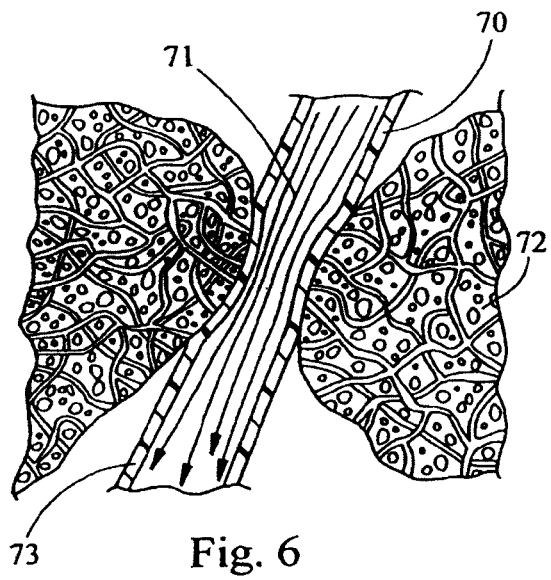
FIG. 6 depicts a stricture in a body lumen.

The procedure described above for dual, coaxial dilatation may be especially useful when there is a stricture or narrowing of a ureter for any reason. FIG. 6 depicts one such case. In FIG. 6, ureter 70 is constrained from its normal width 73 into a narrower path 71 along part of its length by a constricting body mass 72. An example would be a cancerous growth near the ureter that would cause compression on the ureter, e.g., colon cancer, bladder cancer, ovarian cancer, endometrial cancer, cervical cancer, and the like. In such cases, a stent with greater radial strength may be needed in order to maintain its lumen and allow drainage of urine through the ureter. Instead of elastomeric or plastic stents, a stent made from material that is more resistant to deformation may be needed. In addition, the stent must be removable without significant deformation or resistance.

Figure 5:
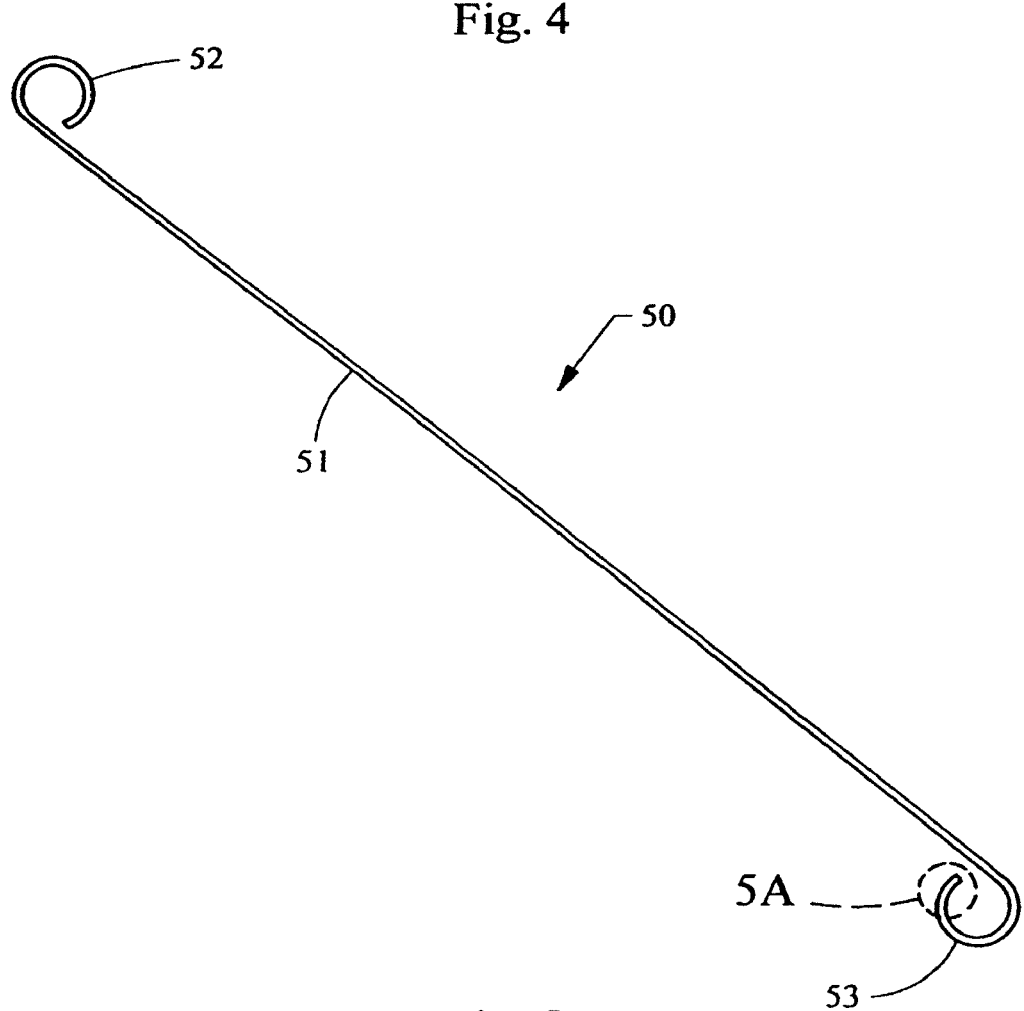
FIGS. 5, 5a and 5b depict a ureteral stent useful in kit embodiments.
Figure 5A:
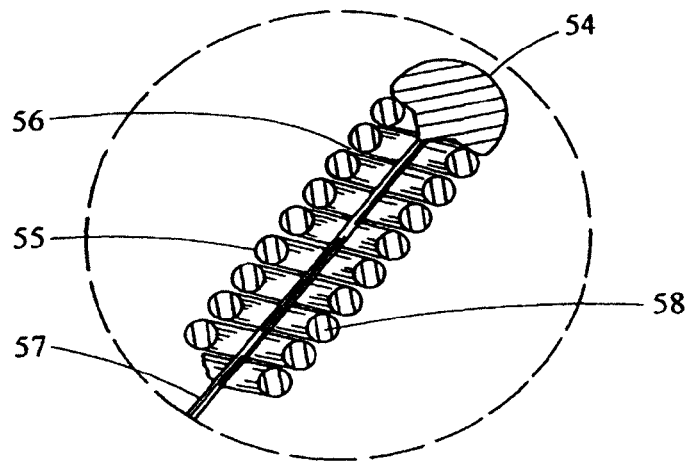
Figure 5B:
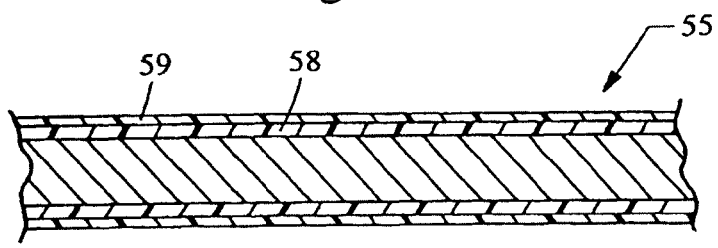

Such a stent is depicted in FIGS. 5, 5a, and 5b. Stent 50 is made from coiled wire along its length 51 and at both distal and proximal ends 52, 53, which may be substantially the same or may be different. The coils should be closely spaced so that they touch, but still allow fluid, such as urine or bile, to flow through the coils. The coils should also be spaced closely enough so that no tissue ingrowth occurs. Materials used in these stents are preferably biocompatible and corrosion-resistant. The wire is preferably made from alloys with minimal or low magnetic properties to avoid interference with diagnostic equipment, such as MRI machines. Alloys such as MP35N, MP 159, Astroloy M, Inconel 625, 316 stainless steel, 35N LT, Biodur 108, pure titanium, and Hastelloy S are preferred.

An inner wire 57 extends throughout the length of the stent and is secured to both ends 52, 53, such as by welding, brazing or swaging to a tip 54 on each end. The tips and the wire are preferably made from the same metallic alloy as the coil. The tips may be formed into a molten domed mass from the coiled wire and the inner wire during the joining process. It is important that both ends be atraumatic to the patient. The coils 55 have small gaps 56 between them so that urine may soak or leak into the stent in the kidney area or anywhere along the ureter and may leak out of the coils in the ureter or bladder area. The internal wire is helpful in preventing unraveling or extension of the coils, especially when the stent is being removed. The portion of the stent between the pigtails is preferably about 20 cm to about 32 cm long. Other lengths may be used.

In order to present a surface highly resistant to encrustation during long-term implantation, stent embodiments should be highly polished, preferably electro-polished. In electro-polishing, the article to be polished is placed into an electrolytic bath, but instead of being plated, the current is reversed. Asperities, tiny projections of metal on the surface of the stent coils, are vulnerable to this process, and are removed without changing the dimensions or temper of the stent. This highly polished surface is believed to be resistant to the bacteria responsible for encrustation because there are fewer sites of surface roughness suitable for adherence.

The wire 55 used for the outer coils is preferably coated, such as with a fluoropolymer or other protective, lubricious coating 58 before it is wound into a coil. It is preferred that the entire coil length be coated, while preserving the small gaps between the coil-turns of the stent for functioning of the stent drainage mechanism. In addition, a layer 59 of a preventive or other medication may be applied over coating 58, such as a layer containing heparin or other drug. Heparin tends to resist encrustation with long-term implantation of urinary tract medical devices. Heparin or other drug-containing coatings are preferably applied after the coil is wound. Fluoropolymers such as PTFE help to enable the bonding of certain drugs, such as heparin, to the surface of the coils and are therefore desirable in stents intended for long-term implantation. Other drugs useful for discouraging encrustation include heparin, covalent heparin, dexamethazone, dexamethasone sodium phosphate, dexamethasone acetate and other dexamethasone derivatives, triclosan, silver nitrate, ofloxacin, ciproflaxin, phosphorylcholine and triemethoprim.

In one preferred embodiment, the wire for coiling is coated, as by extrusion, with a fluoropolymer or other lubricious polymer or plastic material, and is then wound into a coiled stent, complete with end caps and a coated internal wire. The stent is then immersed into a solution of heparin, and a partial vacuum is applied to the vessel containing the solution. Preferred is a vacuum of 10 Torr or less for a time period of about one minute to one hour, depending on the amount of coating desired. The stents are then rinsed in distilled water and dried before being packaged.

Figure 5C:
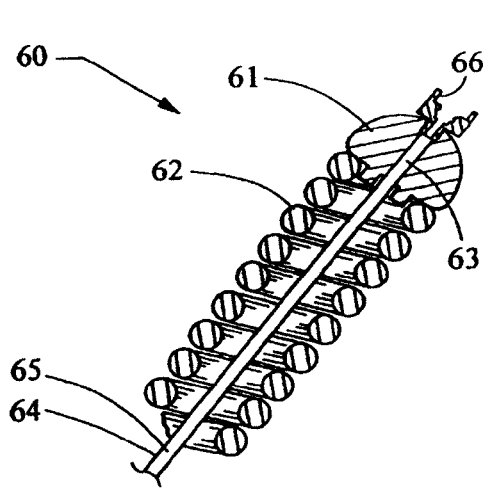
FIG. 5c depicts a second embodiment of a stent.

Another embodiment of a stent with greater radial strength is depicted in FIG. 5c. In this embodiment, which is similar to the embodiment of FIG. 5a, a narrow hollow cannula 64 extends between the distal and proximal ends of the stent 60. Stent 60 includes metallic ends 61 which include an orifice 63 to accommodate cannula 64. The stent includes a hollow outer coil 62 for greater radial strength. Cannula lumen 65 may be used to enable placement by a wire guide, and also may act as a lumen for drainage of body fluids, such as urine or bile. Fluid connector 66 may be attached to a proximal end of the cannula for connection for fluid drainage or for infusion of diagnostic or therapeutic fluids. The fluid connector may be attached by threads, by soldering or brazing, by or by any convenient method.

In addition, one or more additional medications or drugs may be placed on the surface of the stent in order to assist in patient care and comfort. For instance, an antimicrobial drug, such as a combination of rifampin and minocycline, may help to reduce inflammation and microbial activity in the vicinity of the stent. Antimicrobial coatings applied to the stent may include the following drugs, or their salts or derivatives: rifampin, minocycline, a mixture of rifampin and minocycline, a non-steroidal anti-inflammatory agent, a penicillin, a cephalosporin, a carbepenem, a beta-lactam, an antibiotic, an aminoglycoside, a macrolide, a lincosamide, a glycopeptide, a tetracyline, a chloramphenicol, a quinolone, a fucidin, a sulfonamide, a trimethoprim, a rifamycin, an oxaline, a streptogramin, a lipopeptide, a ketolide, a polyene, an azole, an echinocandin, alpha-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, rifampycin, silver, benzyl peroxide, alcohols, and carboxylic acids and salts, and silver sulfadiazine. Also useful as antimicrobials are anthracyclines, such as doxorubicin or mitoxantrone, fluoropyrimidines such as 5-fluoroacil, and also podophylotoxins, such as etoposide. The salts and the derivatives of all of these are meant to be included as examples of antimicrobial drugs.

Analgesics, such as aspirin or other non-steroidal anti-inflammatory drugs, may also be applied to the surface to reduce pain and swelling upon implantation of the stent. These drugs or their salts or derivatives may include aspirin and non-steroidal anti-inflammatory drugs, including naproxen, choline, diflunisal, salsalate, fenoprofen, flurbiprofen, ketoprofen, ibuprofen, oxaprozin, diclofenac, indomethacin, sulindac, acetoaminophen, tolmetin, meloxicam, piroxicam, meclofenamate, mefanimic acid, nabumetone, etodelac, keterolac, celecoxib, valdecoxib and rofecoxib, mixtures thereof, and derivatives thereof.

Other analgesics or anesthetics that may be coated onto the surface of the stent include opioids, synthetic drugs with narcotic properties, and local anesthetics to include at least paracetamol, bupivacaine, ropivacaine, lidocaine, and novacaine.alfentanil, buprenorphine, carfentanil, codeine, codeinone, dextropropoxyphene, dihydrocodeine, endorphin, fentanyl, hydrocodone, hydromorphone, methadone, morphine, morphinone, oxycodone, oxymorphone, pethidine, remifantanil, sulfentanil, thebaine, and tramadol, mixtures thereof, and derivatives thereof.

Any of these drugs and coatings are preferably applied in a time-release manner so that the beneficial effect of the drug is sustained over a period of at least several weeks or months. This may be especially helpful in the case where a stent or catheter will remain in place for a considerable length of time.

Turning now to the embodiments disclosed in FIGS. 10-13, an alternate stent 300 is provided. Stent 300 is made from a first hollow coiled section 310 and a second hollow coiled section 330 disposed within a first lumen 314 defined by the first hollow coiled section 310. First coiled section 310 extends between distal and proximal end portions 311, 312, which may be substantially the same dimensions or orientation or may be different. The plurality of coils 316 that define first coiled section 310 may be closely spaced so that they touch, but still allow fluid, such as urine or bile, to flow through the coils 316 and into the first lumen 314. The coils 316 should be spaced closely enough so that substantially no tissue ingrowth occurs therebetween. The materials used for at least the first and second coiled sections 310, 330 and the finishing and coatings on the wire used to define the first and/or second sections are similar to those discussed with respect to stent 50, discussed above.

A second coiled section 330 is disposed within the lumen 314 defined by the first coiled section 310. The second coiled section 330 extends between distal and proximal end portions 331, 332 which are fixed to the respective distal and proximal ends 311, 312 of the first coiled section 310. Second coiled section 330 may be formed such that the outer diameter thereof is significantly smaller than the diameter of the first lumen 314. The second coiled section 330 defines a second lumen 334 therewithin. The second lumen 334 is formed with an inner diameter that is slightly larger than the diameter of a typical wire guide 17.

Figure 11:
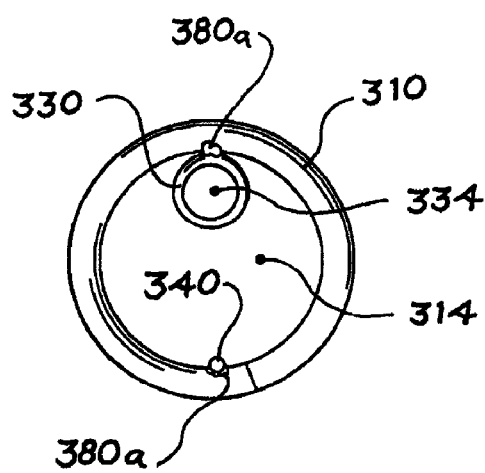
FIG. 11 is an end view of the stent of FIG. 10.
Figure 12:
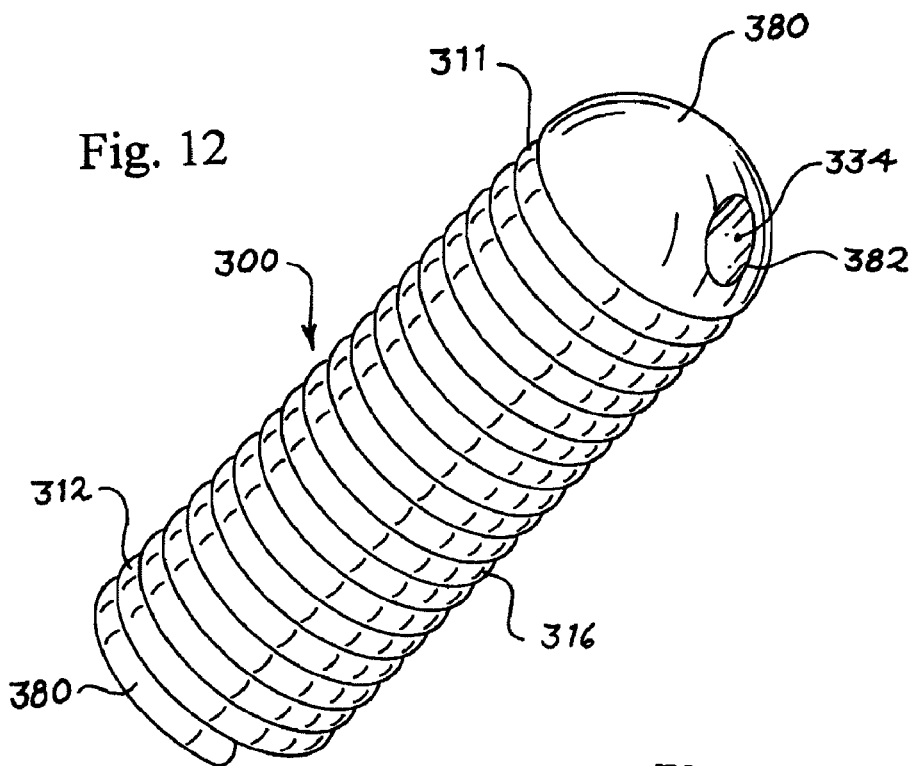
FIG. 12 is a perspective view of an alternate dual lumen ureteral stent.

The first and second coiled sections 310, 330 are fixed together at their respective distal ends 311, 331 and proximal ends 312, 332 so that the second coiled section 330 is fixedly retained within first lumen 314. The respective ends of the first and second coiled sections 310, 330 may be fixed together with one or more weld beads 380, mechanical fasteners, adhesives, or by other methods known to fix similar materials together. In embodiments, where weld beads 380 are provided, the weld beads 380 may extend through substantially the entire diameter of the first coiled section 310 as shown in FIG. 11. Specifically, in embodiments with the second coiled section 330 provided within the lumen 314 within the first coiled section 310, an aperture 382 is provided on the weld beads 380 to provide for communication with the second lumen 334 from either of the distal or proximal ends of the stent 300. Specifically, both the second lumen 334 and the apertures 382 are at least slightly larger than the diameter of a typical wire guide 17 to allow the stent 300 to be threaded along a wire guide 17 for installation into a patient without the use of an access sheath or catheter. In other embodiments shown in FIG. 10-11, the weld beads 380a may be tack welded in a manner to not substantially obstruct access to the second lumen 334 from either end of the stent 300.

Figure 13:
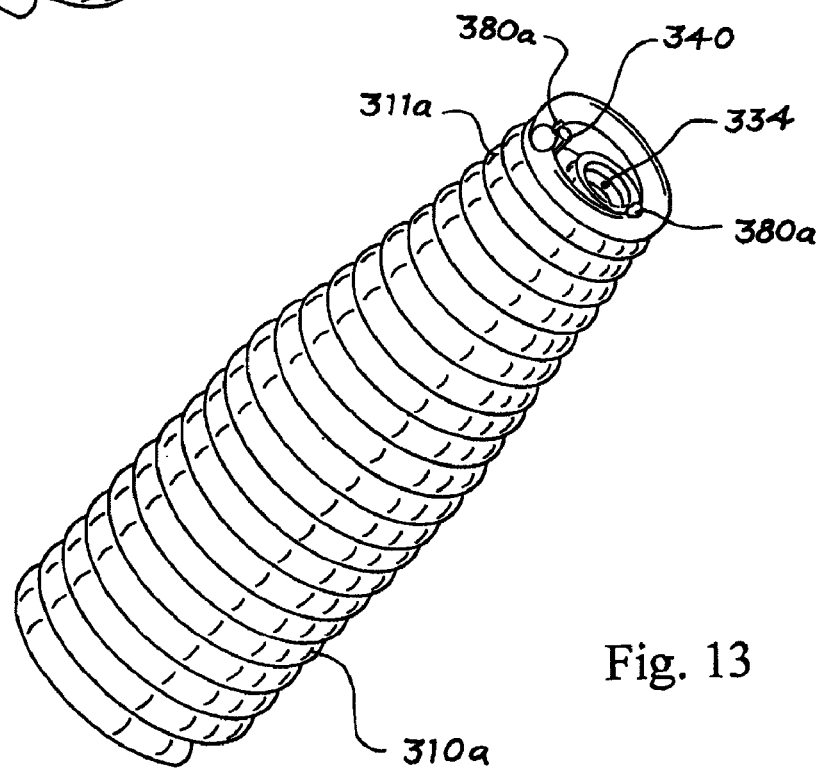
FIG. 13 is a perspective view of another alternate dual lumen ureteral stent.

The weld beads 380 are preferably formed with a curved profile to provide an atraumatic distal end of the stent 300 for placement within the patient. The curved profile substantially prevents or minimizes damage to the surrounding human tissue (such as the ureter) when the stent is inserted within the patient, which may cause subsequent discomfort and/or complications. Further, in some embodiments as shown in FIG. 13, the distal end portion 311a of a first coiled section 310a may be formed with a smaller outer diameter than the remaining length of the first coiled section 310. For example, in some embodiments, the outer diameter of the majority of the first coiled section 310 is approximately 0.079 inches, while the outer diameter of the distal end portion 311a is approximately 0.053 inches. In some embodiments, the taper along the distal end portion 311a may be approximately 10 degrees, in other embodiments, the taper may be between the range of 1 to 45 degrees. The reduced diameter profile of the distal end portion 311a provides for a relatively atraumatic distal end portion 311a to allow for gradually dilating the neighboring tissue when the stent 300 is inserted into the proper position.

In other embodiments, an end cap 61 (FIG. 5c) may be welded onto the distal and proximal end portions 311, 312 of the first coiled section 310, which fixes the second coiled section 330 to the first coiled section 310 and further provides an aperture or orifice 63 therethrough that provides for inserting a wire guide 17 through the end cap 61 and through the second lumen 334.

The stent 300 additionally includes a rod 340 or wire that extends within the first lumen 314 and is fixed to both the distal and proximal ends 311, 312 of the first coiled section 310. The rod 340 may be a thin wire, with any suitable cross-section such that the cross-sectional area of the rod 340 is sufficient to provide sufficient strength to prevent the first and second coiled sections 310, 330 from stretching during the implantation, removal, or the service life of the stent 300 within the patient. In some embodiments, the rod 340 may be a relatively flat wire to minimize the reduction in cross-sectional area of the first lumen 314. The rod 340 may be fixed to the first coiled section 310 with the same weld bead 380 (or other type of fixation structure) that is used to fix the respective distal ends 311, 331 and proximal ends 312, 332 of the first and second coiled sections 310, 330 together, or may be fixed to the first coiled section 310 with a separate weld bead 380a (or other mechanical or chemical process or structure).

The stent 300 further may include deformable pigtail shaped sections on one or both of the distal and proximal ends 311, 312 of the first coiled portion 310 similar to the stent 40 shown in FIG. 4. The pigtail shaped sections 311a, 312a are provided to help maintain the stent 300 in the selected position within the patient's anatomy in certain situations, as well as various other benefits. Because both of the distal and proximal ends 311, 312 include respective pigtail portions, the stent 300 resists significant longitudinal movement through the ureter due to the pigtail's resistance to deformation for the pigtail orientation to the relatively straight orientation required to significantly move the stent 300 through the bodily channel or lumen. Specifically, to remove the pigtail portions from the bodily structure (such as the kidney or bladder), a threshold longitudinal pulling force would be required to urge the pigtails into a relatively linear orientation required to extend through the tubular lumen.

The stent 300 may be fabricated using a plurality of different methods. In a first representative method, the first coiled section 310 is made from a wire that is wrapped in a coiled fashion with a plurality of tightly wound coils 316 that define the first lumen 314. In some embodiments, the plurality of coils 316 is defined by wrapping a wire around a mandrel or similar structure. The plurality of coils 316 defining the first coiled section 310 should be closely spaced so that they touch, but still allow fluid, such as urine or bile, to flow through the coils 316 and so that no tissue ingrowth occurs therebetween. A wire 340 is cut to the same length as the first coiled section 310 and inserted within the lumen 314 until the opposite ends of the wire 340 are aligned with each of the distal and proximal ends 311, 312. The first coiled section and the wire 310, 340 are fixed with a weld 380a or other type of mechanical or chemical joint at each of the distal and proximal ends of both the wire 340 and the first coiled section 310.

A second coiled section 330 is made from a wire that is wrapped in a coiled fashion with a plurality of tightly wound coils 336 to define a second lumen 334. In this embodiment, the second coiled section 330 is made in a separate manufacturing step or process than that used to make the first coiled section 310. The second coiled section 330 may be made by wrapping a wire around a mandrel or similar structure. The second mandrel has a significantly smaller diameter than the mandrel used to make the first coiled section 310, such that the second coiled section 330 can easily be inserted within the lumen 314 of the first coiled section 310 with a significant area for unabated liquid flow through the first lumen 314. The second coiled section 330 may be defined from the same wire used to define the first coiled section 310, or alternatively, the second coiled section 330 could be defined from a smaller gauge wire to minimize the reduction of cross-sectional area of the first lumen 314 available for urine or other liquid flow.

Next, the second coiled section 330 is inserted within the first lumen 314 until the respective distal ends 311, 331 and the respective proximal ends 312, 332 are substantially aligned. The respective ends are then welded together to form a weld bead 380 on each of the distal and proximal ends of the stent 300, or mechanically or chemically fixed together by other methods. In some embodiments, the weld bead 380 may be formed by a localized tack weld 380a. The weld bead 380 or other connection method should be formed to maintain access to the second lumen 334 through each end of the stent 300 so that the stent 300 can be placed over a previously placed wire guide 17. In other embodiments, it is possible to fix one or both distal and proximal ends of the first and second coiled sections 310, 330 with other types of fixation means.

Alternatively, in some embodiments an end cap 61 may be welded or otherwise fixed to the first and second coiled sections 310, 330. The end cap 61 includes an aperture or orifice 63 to provide room for a wire guide 17 to be threaded through the second lumen 334 and the distal and proximal ends of the stent 300.

In an alternate embodiment, the stent 300 may be manufactured by another method. The alternate method provides two mandrels of differing diameters suitable for forming the first and second coiled sections 310, 330 in series from the same length of wire. The two sections are formed around the mandrels to form respective tightly wound coils 316, 336 and are connected together after the plurality of coils 316, 336 are formed by the single strand of wire. Similar to the embodiment discussed above, the second mandrel has a significantly smaller diameter, such that the second coiled section 330 can be inserted within the lumen 314 of the first coiled section 310 with sufficient area remaining within the first coiled section 310 to allow for unabated liquid flow therethrough.

After the first and second coiled sections 310, 330 are wrapped by the wire, the mandrels are withdrawn from within the first and second coiled sections 310, 330 and the free end of the second coiled section 330 (i.e. the end of the second coiled section 330 not directly connected to an end of the first coiled section 310) is inserted through the first lumen 314. The second coiled section 330 is further inserted into the lumen 314 of the first coiled section 310 until the free end of the second coiled section 330 is in proximity of the free end of the first coiled section 310. The two free ends are then welded or otherwise mechanically or chemically connected together. Next, the junction between the first and second coiled sections 310, 330 may be cut and the two cut ends also welded or otherwise mechanically or chemically fixed. Finally, a wire 340 is threaded through the lumen 314 of the first coiled section 310 and opposing ends of the wire are welded or otherwise fixed to the distal and proximal ends 311, 312 of the first coiled section 310.

In still other embodiments, the first and coiled sections 310, 330 may be defined from a single wire by forming the plurality of coils 316 of the first coiled section 310 and the plurality of coils 336 of the second coiled section 330 in an alternating fashion. Next, a wire 340 may be inserted within the first lumen 314 and fixed to each end of the first coiled section 310, as discussed above.

While the present stent is highly useful for drainage of the kidneys, similar stents may be used in other hollow parts of the body. These may include biliary or gall bladder stents, stents for use in percutaneous nephrostomy procedures, hepatic drainage, gastrointestinal drainage, and so on, for drainage of other body cavities. It is intended that the foregoing detailed description be regarded as illustrative rather than limiting, and that it be understood that it is the following claims, including all equivalents, that are intended to define the spirit and scope of this invention.

What is claimed is:

1. A stent comprising:
   a first coiled wire defining a first lumen between a distal end portion and a proximal end portion, the first lumen communicating outside the first coiled wire through small spaces between adjacent coils; and
   a second coiled wire defining a second lumen disposed within the first lumen and secured to the first hollow coiled wire such that an outer surface of the second coiled wire substantially contacts an inner surface of the first coiled wire between the distal and proximal end portions of the first coiled wire;
   further comprising a substantially stretch resistant rod disposed entirely within the first lumen and secured to the distal and proximal end portions, and each of the distal and proximal end portions further comprise an end cap substantially closing the respective end portion, each end cap comprising a single aperture configured to allow a wire guide to extend through the respective aperture and the second lumen, and wherein each end cap restricts yet restrict flow or movement of a component into the remainder of the first lumen not including the second coiled wire.

2. The stent of claim 1, further comprising a distal pigtail portion on the distal end portion of the first coiled wire and a proximal pigtail portion on the proximal end portion of the first coiled wire.

3. The stent of claim 1, wherein the end cap is a weld joint fixing the first coiled wire, the second wire, and a rod disposed within the first lumen.

4. The stent of claim 1, wherein a distal end portion of the second coiled wire is fixed to the distal end portion of the first coiled wire and a proximal end portion of the second coiled wire is fixed to the proximal end portion of the first coiled wire.

5. A kit for placing a stent, the kit comprising:
   a wire guide; and
   a stent for placing in a body passage of a patient, wherein the stent comprises a distal end portion and a proximal end portion, a first coiled wire defining a first lumen, the first lumen communicating outside the coiled wire through small spaces between adjacent coils, and further comprising a second coiled wire defining a second lumen disposed within the first lumen and secured to the first coiled wire such that an outer surface of the second coiled wire substantially contacts an inner surface of the first coiled wire between the distal end portion and the proximal end portion of the stent;
   wherein each of the distal and proximal end portions further comprise an end cap substantially enclosing the respective distal and proximal end portions, each end cap comprising an aperture aligned with the second lumen to allow the wire guide to extend through the aperture and the second lumen, each end cap restricting flow or movement of a component into the remainder of the first lumen not including the second coiled wire, the stent further comprising a substantially stretch resistant internal rod entirely disposed within the first lumen and secured to the distal and proximal end portions of the stent.

6. The kit of claim 5, wherein the distal end portion comprises a distal pigtail portion and the proximal end portion comprises a proximal pigtail portion.

7. The kit of claim 5, wherein the second coiled wire is formed independently of the first coiled wire.

8. The kit of claim 5, wherein the second coiled wire is formed when the first coiled wire is formed.

9. The kit of claim 5, wherein at least the first coiled wire is smoothed by an electropolishing process.

10. The kit of claim 5, further comprising a coating on at least a portion of the first coiled wire, the coating comprising an antimicrobial, antiencrustation, analgesic, or anesthetic compound.

* * * * *